United States Patent [19]
Heimann

[11] Patent Number: 4,969,453
[45] Date of Patent: Nov. 13, 1990

[54] CERVICAL COLLAR

[76] Inventor: Dieter Heimann, Koenigsberger Ring 99, D-2340 Kappeln, Fed. Rep. of Germany

[21] Appl. No.: 221,076
[22] Filed: Jul. 19, 1988
[30] Foreign Application Priority Data Jul. 28, 1987 [DE] Fed. Rep. of Germany ....... 3724885
Jan. 25, 1988 [DE] Fed. Rep. of Germany ....... 8800825
Feb. 2, 1988 [DE] Fed. Rep. of Germany ....... 3800022

[51] Int. Cl.$^5$ ............................................. A61F 5/04
[52] U.S. Cl. ........................... 128/87 B; 128/DIG. 23
[58] Field of Search ......... 128/75, 78, 87 B, DIG. 23, 128/DIG. 15

[56] References Cited
U.S. PATENT DOCUMENTS

| | | | |
|---|---|---|---|
| 460,451 | 9/1891 | Shaw | 128/DIG. 23 |
| 1,051,896 | 2/1913 | Kirkpatrick | 128/75 |
| 1,930,440 | 10/1933 | Longfellow | 128/DIG. 23 |
| 2,088,207 | 7/1937 | Kaiser | 128/DIG. 23 |
| 2,166,229 | 1/1937 | Anderson | 128/DIG. 23 |
| 2,284,058 | 5/1942 | Kaiser et al. | 128/97.1 |
| 2,801,630 | 8/1957 | Moore | 128/87 B |
| 2,807,260 | 9/1957 | Teufel | 128/DIG. 23 |
| 3,224,439 | 12/1965 | Blair, Jr. | 128/DIG. 23 |
| 3,283,755 | 11/1966 | Harden | 128/DIG. 23 |
| 3,364,926 | 1/1968 | Alderson | 128/75 |
| 4,232,663 | 11/1980 | Newton | 128/DIG. 23 |

FOREIGN PATENT DOCUMENTS 1132607  11/1968  United Kingdom ................. 128/75

Primary Examiner—Robert A. Hafer
Assistant Examiner—C. Sam
Attorney, Agent, or Firm—Wells & White

[57] ABSTRACT

A cervical support to immobilize the cervical vertebral column is in the form of a padded collar enclosing the patient's neck and so designed that individualized immobilization is possible within a limited region of the head, as required in a number of indications, for instance in wear phenomena in the cervical vertebral column zone or in post-operation treatment.

For that purpose the invention provides that the cervical support comprise a clearance in its front region with a flexible frame comprising spacers between its upper and lower bounds that can be shifted along the clearance.

11 Claims, 5 Drawing Sheets

CERVICAL COLLAR

BACKGROUND OF THE INVENTION

The invention concerns a cervical support to immobilize the cervical vertebral column, in the form of a padded collar enclosing the patient's neck.

Known cervical supports of this kind (U.S. Pat. No. 4,099,523) consist of two mutually displaceable rigid segments with adjustable spacing, on one hand to match the cervical support to different body shapes and on the other hand to apply some pressure on the head parts to be supported so as to relieve the cervical vertebral column.

A drawback is however incurred in that the known cervical supports support the head only as a whole; a partial support matched to the particular case is impossible with the known cervical supports.

SUMMARY OF THE INVENTION

Accordingly it is the object of the invention to so design a cervical support of the initially cited kind that it shall allow individual immobilization over a restricted region of the head, as is required in a plurality of indications, for instance for wear phenomena in the region of the cervical vertebral column or in post-operation treatment.

This problem is solved by the invention in that the cervical support comprises at its front a clearance with a flexible frame including spacers between its upper and lower bounds and displaceable along this clearance.

In this design, the cervical support is incompressible, or only insignificantly where the spacers are located. These immobilizing regions can be selected for the individual by shifting the spacers along the clearance. The cervical support is extensively deforming where the spacers are absent and thereby assures optimal freedom of motion into the particular pain-free direction.

One or more spacers may be provided, four spacers being appropriate. However there may be circumstances where a single spacer in the cervical support of the invention suffices to achieve the desired effect. The spacers may be elastic and lockable.

Appropriately the clearance extends over at least 180° when the cervical support is closed, and where called for it may be made even larger. The closure of the cervical support, typically of the VELCRO type, is located between the mutually facing ends of the clearance.

Appropriately the flexible frame may be in the form of a flat plastic strip padded on the outside.

Especially appropriately, the flexible frame is reinforced on its inside by a peripheral wire engaged by the spacers. This wire can be held against the frame in displaceable manner by slotted clamps in view of a relative motion between wire and frame taking place when the support is compressed. Moreover the wire frame may be open in the vicinity of one end so that the free ends thus formed can be inserted into openings in the frame.

The spacers may be in the form of turnbuckles, that is consisting of one nut and two opposite threads and two screws secured against rotation and acting on the frame.

Especially advantageously however the spacers themselves also will be merely made of spring wire because thereby it is possible to make the cervical support very light-weight. In particular appropriate manner, the spring wire shall be approximately semi-circular and this semi-circle shall have a diameter corresponding to the height of the clearance between the wire segments in the rest position.

The ends of the spacer can be joined by welding or soldering to the peripheral wire.

The spacers may be provided at their ends facing the frame segments with apertures or the like admitting tenons or the like. Thereby the particular spacer may be detached in simple manner merely by pulling apart the frame segments and then may be shifted into another position in the clearance.

Especially advantageously, the wire reinforcing the frame shall be equipped with projections, tenons and bulges or the like pointing inward toward the clearance which in the operative state enter matching recesses of the spacers. In order to fix the positions, the inward surfaces of the tenons may comprise snap-in channels cooperating with corresponding bearings at the ends of the spacers.

Because of the individual adjustability of the cervical support of the invention, same where called for also may be so shaped that the head shall be totally immobilized, i.e. that bilateral immobility will ensue because spacers are mounted on both sides of the head, i.e. on the mutually opposite sides of the support.

The design of the cervical support of the invention with such a comparatively large clearance offers moreover the advantage that no feeling of pressure and heat can arise in the front neck region. Unlike the other parts of the cervical support, the clearance in this respect appropriately is not covered by padding but by a thin lining permeable to air.

The cervical support may be symmetrical, whereby it need merely be reversed in order to shift a spacer.

BRIEF DESCRIPTION OF THE DRAWINGS

The invention is discussed below in relation to illustrative embodiments shown in the drawing.

DESCRIPTION OF THE PREFERRED EMBODIMENTS

Figure 1:
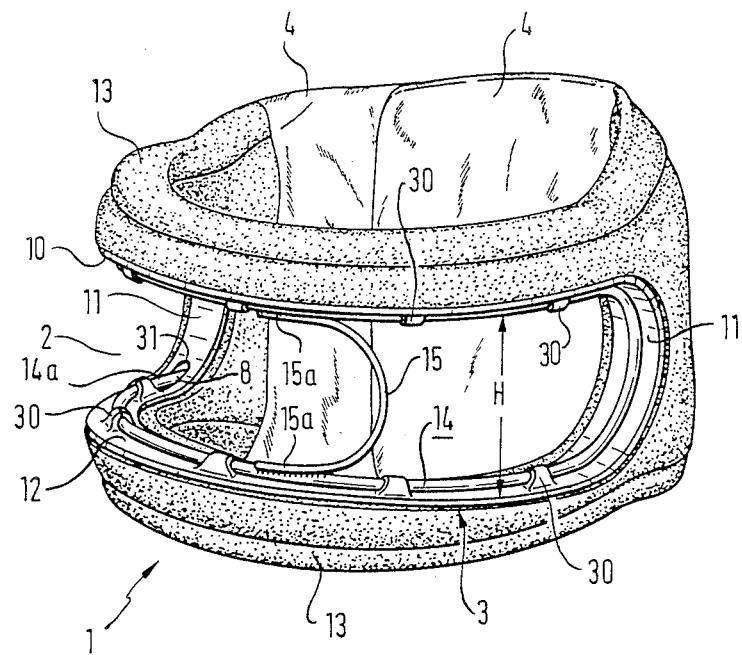
FIG. 1 is a perspective of an embodiment of the cervical support of the invention.

As shown in FIG. 1, the cervical support 1 comprises a clearance 2 which in the operative condition of the support is present in the region facing the front neck region of the wearer. The clearance 2 is provided with a flexible frame 3 comprising an upper frame segment 10 and a lower frame segment 12, which are joined together at their ends by arcs (or arcuate segments) 11. In the embodiment shown in FIG. 1, the frame 3 is in the form of a flat plastic strip.

Accordingly the clearance 2 is compressible.

The frame segments 10 and 12 are provided on their upper and lower sides with soft padding 13, preferably foam.

Two closing strips 4 join the region of the cervical support 1 comprising the clearance 2 and are provided at their mutually overlapping ends each with part of a VELCRO lock.

The flexible frame 3 is reinforced in the embodiment shown by a peripheral elastic wire 14 which herein is acted on by a spacer 15 consisting of a wire bent into a half-circle and which is connected at its engagement points 15a to the frame reinforcing wire 14, preferably by a soldering junction.

The semi-circle of the spacer 15 has a diameter corresponding to the height H of the clearance between the wire segments in the rest position.

In the embodiment mode of FIG. 1, the wire 14 is held in displaceable manner by slotted clamps 30 overlapping it, in view of a relative motion taking place between wire and frame when the support, and hence the clearance 2, is compressed.

The wire frame 14 may be open in the region of one end of the clearance 2, whereby the free ends 14a so formed can be inserted into apertures 31 of the frame 3.

Figure 2:
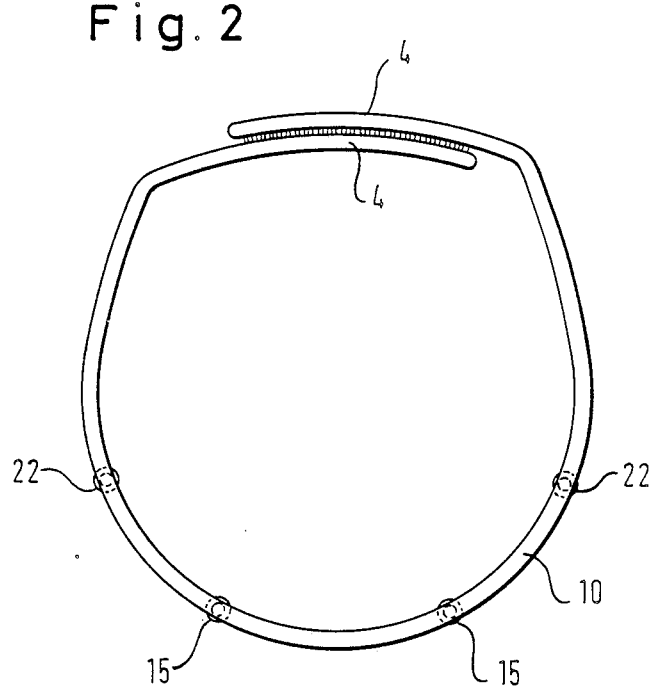
FIG. 2 is a topview of the cervical support of FIG. 1 for a modified embodiment.
Figure 3:
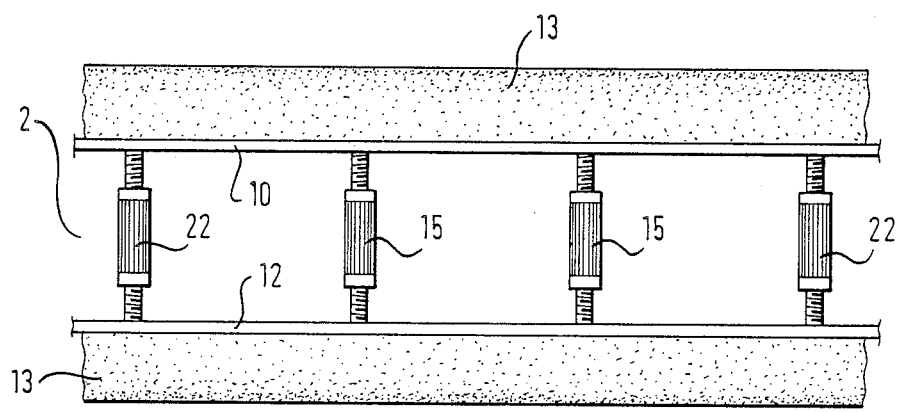
FIG. 3 is a geometric development of a cutaway of the clearance of the cervical support of FIG. 2.

FIGS. 2 and 3 show a modified embodiment, FIG. 2 being a topview of the cervical support and FIG. 3 being a cutaway of the clearance 2. In this case four spacers 15 and 22 are provided, which may each be turnbuckle, that is, they may consist of one nut with two opposite threads and of two irrotational screws acting on the frame. The spacers 15 are so arranged in the embodiment of FIG. 3 that they are present in the region of the mandible angle, whereas the spacers 22 are located in the mastoid zone below the ears. By adjusting the turnbuckles, the cervical support can be adjusted in such a manner that the head shall always be supported in the particularly desired position.

Figure 4:
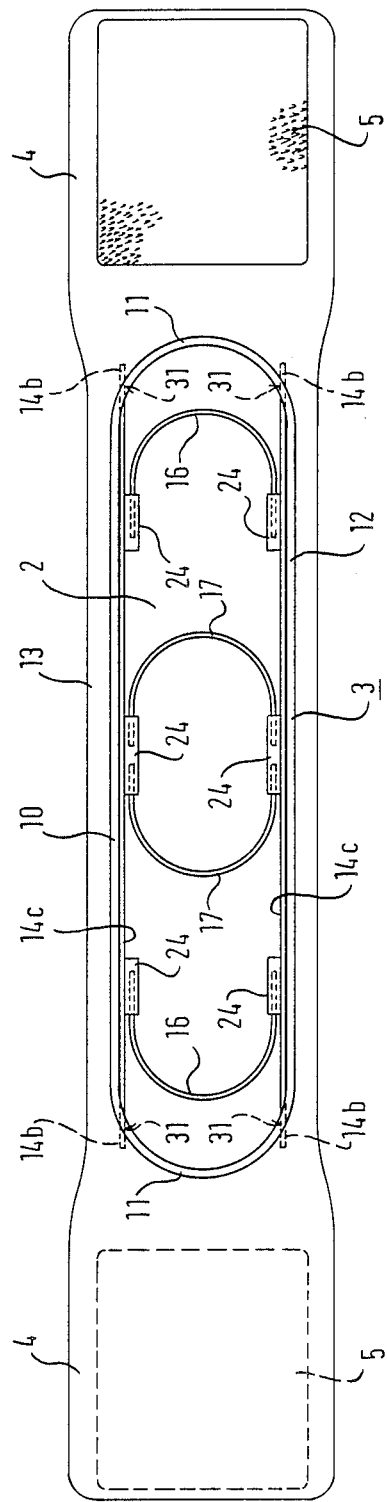
FIG. 4 is a geometric development of the clearance of the cervical support for a modified embodiment.

FIG. 4 shows the geometric development of the clearance 2 of the cervical support for a further embodiment mode. In this case again two semi-circular spring-wire spacers 16 are present in the end zones of the clearance and two further spacers 17 in its midst. These spacers are seated in hollow bodies such as tubes 24 or the like, which may be made of plastic or metal, and which receive the ends of the spacers 16 and 17.

The arrangement of FIG. 4 also comprises, like that of FIG. 3, four spacers associated with specific head locations.

As further shown by FIG. 4, the wire 14 reinforcing the flexible frame may consist of two single parts 14c which are bent in semi-circular shape to correspond to the cervical support but which have each two free ends 14b that can enter corresponding apertures 31 of the frame 3.

Figure 5:
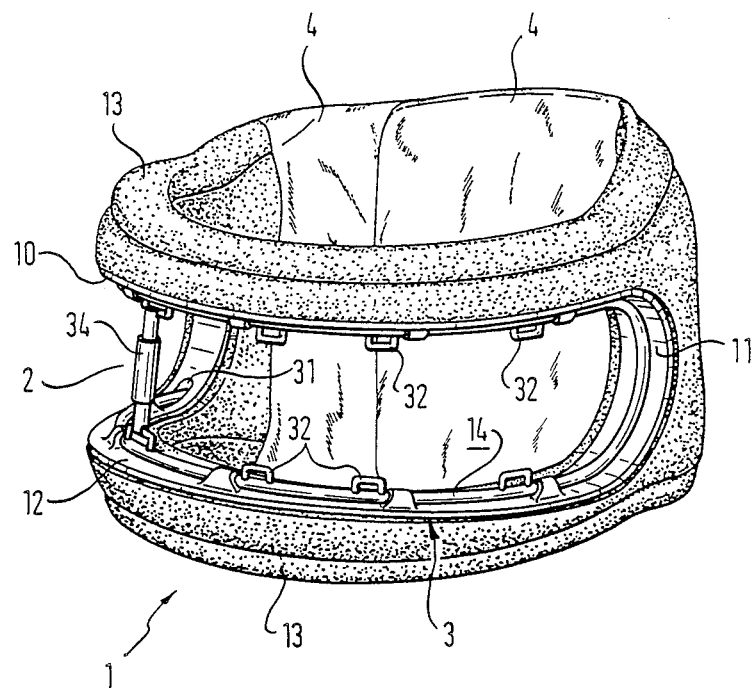
FIG. 5 shows the cervical support of another embodiment but similar to FIG. 1.

FIG. 5 shows a perspective of a further embodiment of the cervical support of the invention. In this embodiment, the wire 14 reinforcing the frame 3 is provided with inwardly pointing projections, tenons 32, bulges or the like which in the operative condition of the support engage matching recesses 33 (see also FIG. 6) of the spacers 34. These tenons 32 may be longer than shown in this Figure, whereby the position of the spacers 34 may be precise within millimeters. For that purpose the inward surfaces 35 of the tenons 32 may be provided with snap-in channels 35 or the like engaging matching bearings.

Figure 6:
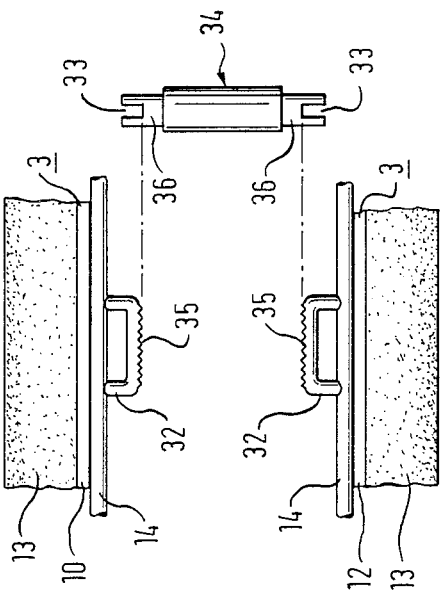
FIG. 6 is an embodiment mode to detachably fix in place the spacers between the upper and lower frame segments of the clearance of the cervical support.

FIG. 6 clarifies the design of such a system. The particular spacer 34 comprises two fork-like ends 36 with clearances 33 which in the operative state overlap the tenons 32 and can be locked against the snap-in channels 35. The ends 36 may be designed for that purpose in such a way that in addition some clamping is exerted on the tenons 32.

Figure 7:
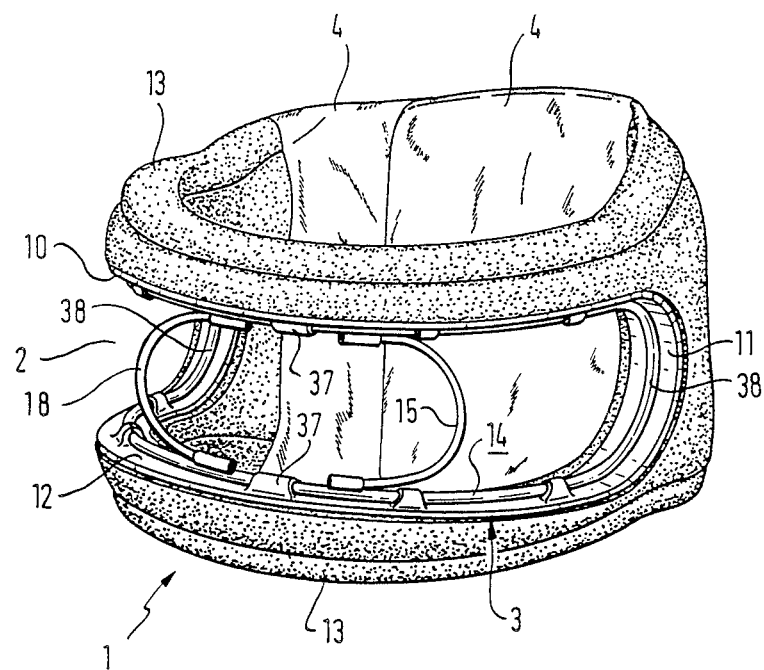
FIG. 7 shows the cervical support in a further embodiment similar to those of FIGS. 1 and 5.

Lastly FIG. 7 shows an embodiment similar to FIG. 1 where a further spacer 18 is present besides the spacer 15. FIG. 7 also shows that the peripheral wire 14 consists of two U-shaped bails of which the free ends enter bushes 37. Similar bushes are entered by the free ends of the spacers 15 and 18 (see FIG. 4).

Because connecting arcs 38 are present in the vicinity of the two ends of the clearance 2 which as such cannot be compressed, and because furthermore the two spacers 15 and 18 are present at the center, such a support is incompressible and thereby acts in immobilizing manner. In the embodiment mode of FIG. 1 on the other hand, the free ends of the spring wire 14 are displaceable relative to each other, whereby motion is possible in that region.

I claim:

1. A cervical collar to immobilize the cervical vertebral column, comprising:
a padded collar member for closure about a patient's neck having a cervical support (1) in the front of said collar member, said cervical support comprising a flexible frame (3) of continuous flat material having upper and lower segments interconnected by a pair of arcuate segments (11), wherein a clearance (2) is defined between the upper segment, the lower segment, and the arcuate segments in said front of said collar member, and supporting spacing means mounted between said upper and lower segments and displaceable along said clearance (2).

2. The cervical collar of claim 1, wherein said supporting spacing means comprise a single spacer.

3. The cervical collar of claim 1, wherein said supporting spacing means comprise a plurality of spacers.

4. The cervical collar of claim 3, wherein said clearance (2) extends over at least 180° of said padded collar member.

5. The cervical collar of claim 4, wherein said collar member has a closure (5) located between two ends of said clearance (2).

6. The cervical collar of claim 5, wherein said flexible frame (3) is a flat strip of plastic with padding (13) on its outside.

7. The cervical collar of claim 6, wherein said flexible frame (3) is reinforced on its inside by a peripheral elastic wire (14) engaged by said spacers (34).

8. The cervical collar of claim 7, wherein said peripheral elastic wire (14) is held to said frame (3) by slotted clamps (30) overlapping said wire.

9. The cervical collar of claim 8, wherein said peripheral elastic wire has free ends (8) entering apertures (31) of said frame (3).

10. The cervical collar of claim 9, wherein said spacers (15,22) are in the form of turnbuckles having one nut with two opposite threads and of two irrotational screws which act on said frame (3).

11. The cervical collar of claim 7, wherein said peripheral elastic wire (14) reinforcing said frame (3) comprises projections pointing inward toward said clearance (2), which in the operative condition of said support enter matching recesses (33) of said spacers (34).

* * * * *